US006585996B1

(12) United States Patent
Lonsdale et al.

(10) Patent No.: US 6,585,996 B1
(45) Date of Patent: Jul. 1, 2003

(54) LIPID-SOLUBLE THIAMINE DERIVATIVES IN THE TREATMENT OF AUTISM

(75) Inventors: Derrick Lonsdale, Strongsville, OH (US); James P. Frackelton, Westlake, OH (US)

(73) Assignee: Westlake Laboratories, Inc., Westlake, OH (US)

( * ) Notice: Subject to any disclaimer, the term of this patent is extended or adjusted under 35 U.S.C. 154(b) by 0 days.

(21) Appl. No.: 10/097,914

(22) Filed: Mar. 13, 2002

(51) Int. Cl.[7] .................................................. A61K 9/00
(52) U.S. Cl. ...................... 424/433; 424/433; 424/436; 424/443; 424/449; 424/451; 424/464
(58) Field of Search ................................ 424/433, 436, 424/443, 449, 451, 464

(56) References Cited

U.S. PATENT DOCUMENTS

| | | | |
|---|---|---|---|
| 3,016,380 A | 1/1962 | Yurugi et al. |
| 4,136,162 A | 1/1979 | Fuchs et al. |
| 4,277,465 A | 7/1981 | Kamada |
| 4,338,306 A | 7/1982 | Kitao et al. |
| 4,479,932 A | 10/1984 | Bodor |
| 5,017,564 A | 5/1991 | Makino et al. |
| 5,152,994 A | 10/1992 | Lotsof |
| 5,215,758 A | 6/1993 | Krishnamurthy |
| 5,516,526 A | 5/1996 | da la Torre |
| 5,843,469 A | 12/1998 | McEntee |
| 5,885,608 A | 3/1999 | McEntee |
| 6,197,746 B1 | 3/2001 | Beck et al. |

OTHER PUBLICATIONS

Mimori et al, "Thiamine Therapy in Alzheimer's Disease", Metabolic Brain Disease, vol. 11, No. 1, pp. 89–94, (1996).*
Motonori Fujiwara, "Absorption, Excretion and Fate of Thiamine and its Derivatives in Human Body", Tokyo, Japan, Igaku Shoin Ltd., 1965, pp. 179–212.

D.G. Wells, M.J.S. Langman, J. Wilson, "Thiocyanate Metabolism in Human Vitamin B12 Deficiency", Brit. Med. Journal, 1972, 4, pp. 588–590.

Derrick Lonsdale, "Effect of Thiamine Tetrahydrofurfuryl Disulfide on Audiogenic Seizures in DBA/2J Mice", Dev. Pharmacol. Ther. 1982, 4, pp. 28–36.

Derrick Lonsdale, "Thiamine and its Fat Soluble Derivatives as Therapeutic Agents", Int. Clin. Nutr., Rev. 7, 1987, pp. 114–125.

Derrick Lonsdale, "Clinical Use of Water Soluble Thiamine and its Fat Soluble Derivative, Thiamine Tetrahydrofurfuryl Disulfice (TTFD)", Int. Journal Biosoc. Res. 1987, 9, pp. 144–152.

B. Rimland, E. Callaway, P. Dreyfus, "The Effective of High Doses of Vitamin B6 on Autistic Children: A Double–Blind Crossover Study", Am. Journal Psychiatry 1978, 135, pp. 472–475.

K. Horvath, K.A. Stafanatos, K.N. Soloski, et al., Abstract of "Improved Social and Language Skills After Secretin Administration in Patients with Austic Spectrum Disorders", Journal Assoc. Minor Phys. 1998, 9(1).

(List continued on next page.)

Primary Examiner—Carlos A. Azpuru
(74) Attorney, Agent, or Firm—Watts, Hoffmann, Fisher & Heinke, Co., L.P.A.

(57) ABSTRACT

The present invention is directed to a method for the treatment of autism comprising administering to a person in need of such treatment a therapeutically effective amount of a lipid-soluble thiamine derivative. The lipid-soluble thiamine derivative is preferably tetrahydrofurfuryl disulfide (TTFD). TTFD administration methods may include suppository forms, transdermal carriers, such as gels, lotions, or creams; and oral carriers, such as tablets or capsules.

14 Claims, 3 Drawing Sheets

OTHER PUBLICATIONS

Derrick Lonsdale, Raymond J. Shamberger, "A Clinical Study of Secretin in Autism and Pervasive Developmental Delay", Journal Nutritional & Environmental Medicine 2000, 10, pp. 271–280.

R.H. Waring, J.M. Ngong, L. Klovrza et al., "Biochemical Parameters in Autistic Children", Dev. Brain Dysfunct. 1997, 10, pp. 40–43.

R.H. Waring, L.V. Klovrza, "Sulphur Metabolism in Autism", Journal of Nutritional & Environmental Medicine 2000, 10, pp. 25–32.

Allan D. Thomson, Oscar Frank, Herman Baker, et al., "Thiamine Propyl Disulfide: Absorption and Utilization", Annals of Internal Medicine 1971, vol. 74, pp. 529–534.

J.R. Cooper and J.H. Pincus, "The Role of Thiamine in Nervous Tissue", Neurochemical Research 1979,(4), pp. 223–239.

Takeshi Fujita and Ziro Suzuoki, "Enzymatic Studies on the Metabolism of the Tetrahydrofurfuryl Mercaptan Moiety of Thiamine Tetrahydrofurfuryl Disulfide", Journal Biochem. 1973, vol. 74, pp. 717–722.

Takeshi Fujuita, Akio Teraoka and Ziro Suzuoki, "Enzymatic Studies on the Metabolism of the Tetrahydrofurfuryl Mercaptan Moiety of Thiamine Tetrahydrofurfuryl Disulfide", Journal Biochem. 1973, vol. 74, pp. 739–745.

Takeshi Fujita and Ziro Suzuoki, "Enzymatic Studies on the Metabolism of the Tetrahydrofurfuryl Mercaptan Moiety of Thiamine Tetrahydrofurfuryl Disulfide", Journal Biochem. 1973, vol. 74, pp. 733–738.

Takeshi Fujita, Ziro Suzuoki, Seizi Kozuka and Shigeru Oae, "Enzymatic Studies on the Metabolism of the Tetrahydrofurfuryl Mercaptan Moiety of Thiamine Tetrahydrofurfuryl Mercaptan Moiety of Thiamine Tetrahydrofurfuryl Disulfide", Journal of Biochem. 1973, vol. 74, pp. 723–732.

S. Kikuchi, K. Nishikawa and Z. Suzuoki, "The Metabolism of Thiamine Tetrahydrofurfuryl Disulfice in the Rat, Rabbit and Man", European Journal of Pharmacology 1970, vol. 9, pp. 367–373, North–Holland Publishing Co., Amsterdam.

David Quig, "Cysteine Metabolism and Metal Toxicity", Alternatie Medicine Review, Aug. 1998, 3, pp. 262–270.

H. Baker, O. Frank, Absorption, Utilization and Clinical Effectiveness of Allithiamines Compared to Water–Soluble Thiamines. Journal Nutr. Sci. Vitaminol., 22 (Suppl.) 1976, pp. 63–68.

Derrick Lonsdale, "A Nutritionist's Guide to the Clinical Use of Vitamin B–1", Chapters 3–4, pp. 44–115, 1987.

* cited by examiner

LIPID-SOLUBLE THIAMINE DERIVATIVES IN THE TREATMENT OF AUTISM

FIELD OF THE INVENTION

The present invention relates to pharmaceuticals and, more specifically, using pharmaceuticals to treat autism.

BACKGROUND OF THE INVENTION

Autism is a disabling neurological disorder that affects thousands of Americans and includes a number of subtypes, with various assumed causes and few documented ameliorative treatments. Autism is characterized by behavioral syndrome often recognized between two and three years of age. There is no clear-cut biological marker for autism. Diagnosis of the disorder is made by considering the degree to which the child matches the behavioral syndrome, which is characterized by poor communicative abilities, peculiarities in social and cognitive capacities, and maladaptive behavioral patterns.

There currently is no known medical treatment for autism. A number of different therapies have been attempted in an effort to cure autism or at least lessen its symptoms, including drug therapies as well as psychiatric care and attempted counseling. In general, results of such treatments have been disappointing, and autism remains very difficult to effectively treat, particularly in severe cases.

In 1951, scientists in Japan discovered that garlic bulbs contained a disulfide derivative of thiamine that was, biologically, a very active form. Scientists noted that this disulfide passes through the lipid barrier in cell membranes, hence, it is referenced to as fat soluble. This lipid soluble form of thiamine was shown to be more readily absorbed from the intestine to produce higher levels of thiamine in the blood, cerebrospinal fluid, and urine, and to induce less thiamine fecal loss than the water-soluble forms of thiamine.

A variety of lipid-soluble thiamine compounds, known as thiamine alkyl disulfides or allithiamines, have been synthesized and are commercially available in Japan, parts of Europe, and elsewhere. The lipid-soluble thiamines most commonly used on humans include thiamine tetrahydrofurfuryl disulfide (TTFD), thiamine propyl disulfide (TPD), and O-benzoylthiamine disulfide.

The lipophilic character of the lipid-soluble thiamines allows these compounds to pass through the membranes of cells, thus allowing a greater amount of thiamine to be introduced into the cell versus the water-soluble form of thiamine. The water soluble forms of thiamine require an enzymatic system to transport it through cell membranes, thus, making the water soluble form less efficient than the lipid soluble form.

Lipid-soluble thiamines have been used on humans on an experimental basis to investigate the short-term treatment of disorders of thiamine deficiency and thiamine metabolism.

There remains a need in the art for a pharmaceutical treatment offering clinical improvement in the autistic patient.

DISCLOSURE OF THE INVENTION

The present invention features a method of treating autism in a patient. The method comprises the step of administering to a person in need of such treatment a therapeutically effective amount of a lipid-soluble thiamine derivative. In one embodiment, the lipid-soluble thiamine derivative is tetrahydrofurfuryl disulfide.

According to one method, the lipid-soluble thiamine derivative is administered rectally in the form of a suppository. In an alternative method, the lipid-soluble thiamine derivative is administered parenterally. Parenteral administration allows for the thiamine derivative to enter the blood stream without being processed through the digestive tract. Parenteral administration can be accomplished by administering the lipid-soluble thiamine derivative transdermally by applying a transdermal carrier substance to the skin and rubbing the composition into the skin. The transdermal composition can be in the form of a gel, lotion, cream or any other transdermal composition as known to those skilled in the art. In yet another alternative method, parenteral administration can be accomplished by administering the lipid-soluble thiamine derivative sublingually.

Other methods of administering lipid-soluble thiamine derivatives, include but are not limited to, administering the lipid-soluble thiamine derivatives orally in the form of a tablet or capsule and administering intravenously. The present invention also contemplates other physiologically acceptable carriers or excipients for carrying an effective amount of the lipid-soluble thiamine derivative into the patient's body.

In a preferred aspect of the instant invention, the method of treating autism comprises administering a lipid-soluble thiamine derivative, in particular, tetrahydrofurfuryl disulfide, to a child in need of such treatment. In yet another embodiment, the lipid-soluble thiamine derivative is administered to a child in need of such treatment in the form of a suppository.

Figure 1:
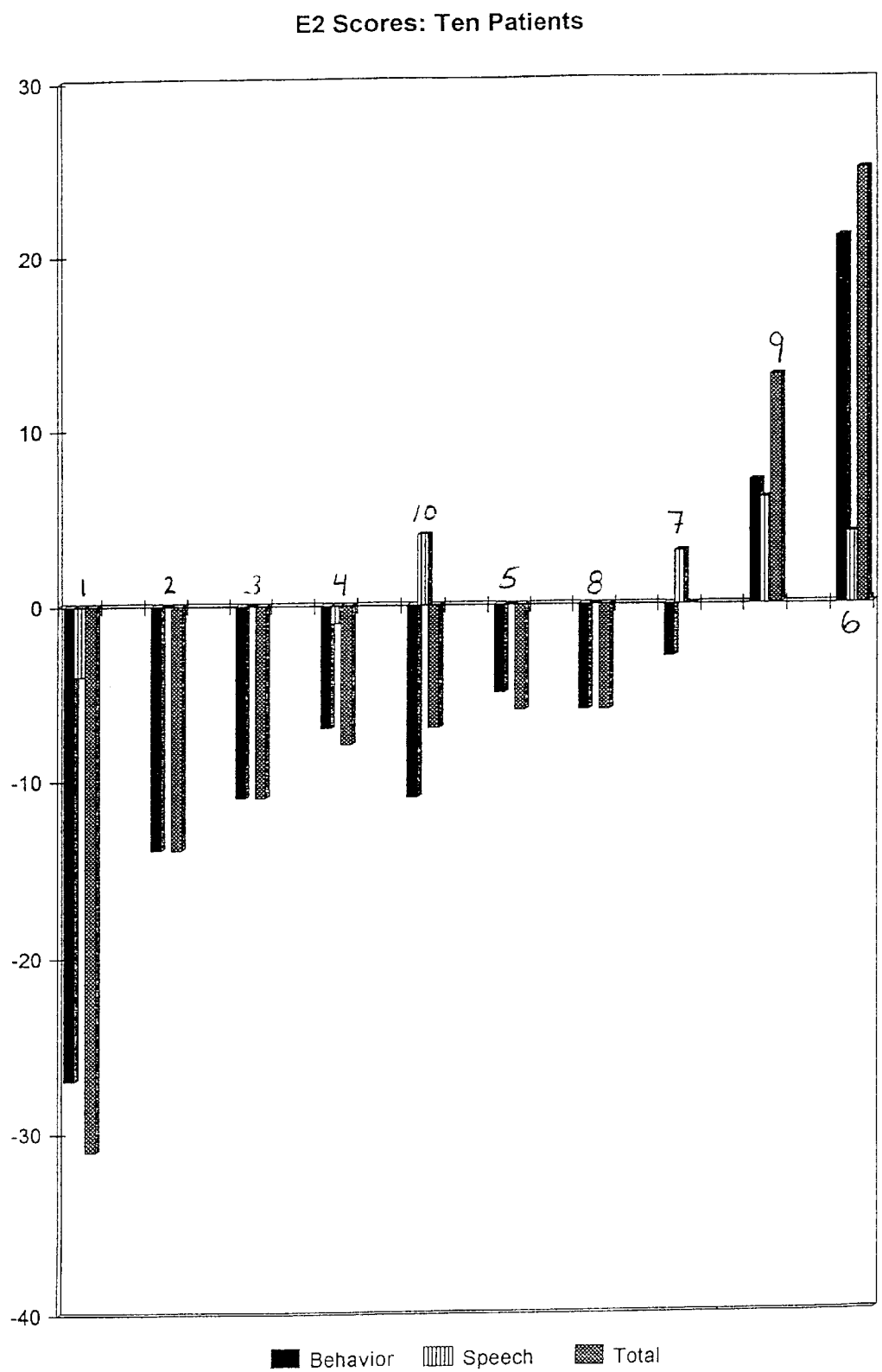
FIG. 1 is a graph of the results of a pilot study involving 10 patients. The graph shows the patients results from the E2 diagnostic form.

The numbers in each of the figures corresponds to the individual patients as listed numerically in Table III.

DETAILED DESCRIPTION

The present invention relates to a method of treating autism comprising administering a pharmaceutically effective amount of a lipid-soluble thiamine derivative to a person in need of such treatment. In a preferred embodiment, the lipid-soluble thiamine derivative is tetrahydrofurfuryl disulfide (TTFD). Tetrahydrofurfuryl disulfide is used in this invention due to its therapeutic properties. Although not wanting to be bound by theory, it is believed that the use of lipid-soluble thiamine derivatives, particularly tetrahydrofurfuryl disulfide, activates rhodanese in the liver. The activation of rhodanese in the liver is explained in Biochemical Parameters in Autistic Children, *Dev. Brain Dysfunction*, 1997; 10:40–43, hereby incorporated by reference in its entirety.

While not wanting to be bound by theory, it is believed that the oxidation of cysteine andmethionine is the major source of sulfate. Cysteine dioxygenase catalyzes the formation of cysteine sulfonic acid, which undergoes transamination and degradation to form sulfite ions. Sulfite ions can then be oxidized to sulfate. As sulfate levels decrease, the synthesis of these bio-components is less adequate and the resorption of the anions becomes less effective. It is believed that this increase in urinary sulfate may partly explain low plasma sulfate levels. Reduced S-oxidation and sulfation appear to have a clinical link with autoimmune dysfunction, suggesting that this might be a factor in many cases of autism. Reduced sulfation has also been associated with inflammation and gut dysfunction.

It is also believed that gastrin is more active when sulfated in a tyrosine residue. This also appears to be true of cholecystokinin, which is active in the brain and the gastrointestinal tract. The secretion of cholecystokinin and production of peptides, liberated by the influences of gastrin and hydrochloric acid in dietary proteins, induces release of secretin, now known to have a beneficial effect in the treatment of some autistic children. Although not wanting to be bound by theory, it is believed that the abnormal release of secretin in these children is due to the underlying abnormality in sulfate metabolism.

In the present invention, although not wanting to be bound by theory, it is believed that the reported significant decrease in urinary thiocyanate plays a role in the autistic condition. This, together with the raised levels of urinary thiosulfate, suggests reduced activity of the enzyme rhodanese. This enzyme detoxifies cyanide ions by combining with thiosulfate to form thiocyanate. Cyanide ions are toxic since they inhibit oxidative phosphorylation or cellular respiration, thereby reducing the supply of ATP. It is believed that the partial deactivation of rhodanese may play a part in the etiology of autism, causing accumulation of cyanide ions. The inventors propose that the use of TTFD causes an increase in the activation of rhodanese in the liver, which rids the body of the accumulation of cyanide ions, thus producing a treatment for autism.

In a preferred embodiment of the present invention, a lipid-soluble thiamine derivative is administered rectally in the form of a suppository. The use of a suppository is an unexpectedly effective treatment for autistic children. Lipid-soluble thiamine derivatives, specifically tetrahydrofurfuryl disulfide, are usually administered orally to treat thiamine deficiency. However, small children are unable to swallow the capsules containing the lipid-soluble derivatives. As a result, the capsules have to be opened and then the powder is administered. Due to the foul taste, children instantly rejected the powder, often by vomiting. To overcome this problem the lipid-soluble thiamine derivative is incorporated into a suppository and given rectally to the autistic child.

When given rectally to a small number of autistic children in a pilot study, consistent results were obtained. Parents noticed a "skunk like" odor either from the child's stool or, in some cases, the child's sweat or urine. This "skunk like" odor is caused by a series of sulfur containing substances known as mercaptans. This result is consistent with what is expected of sulfur containing compounds. Clinical improvements have been observed in these children and are supported by the fact that nearly all of the children have been shown to have increased levels of arsenic in their urine. Arsenic is a sulfhydryl reactive metal, therefore, the production of a mercaptan, evidence of the reaction between arsenic and the sulfhydryl group, strongly suggests the innovative process detoxifies and extracts this poisonous metal.

In yet another preferred embodiment, the lipid-soluble thiamine derivative is administered parenterally. Parenteral administration is characterized by administration in which the pharmaceutical enters the blood stream without going through the digestive canal. Parenteral administration can be accomplished by intravenous, intramuscular, subcutaneous, transdermal (e.g., a gel, lotion or cream) or sublingual administration. Rectal administration is accomplished by incorporating TTFD into a suppository. The suppository can be made by any means known in the art. Suppositories, for the purpose of this invention, contain, for example, about 50 mg of TTFD each. Other forms of parenteral administration are also contemplated by the present invention and would be apparent to one of ordinary skill in the art in view of this disclosure.

The inventors believe that parenteral administration, specifically rectal and transdermal administration, has a biochemical advantage over other forms of administration. For example, when TTFD is given orally, the "skunk like" odor is not readily observed. As noted earlier, the "skunk like" odor appears to be a sign of the activity of the administration of TTFD. In addition, oral administration does not appear to give as striking clinical results as rectal administration. Oral administration does not appear to have the same biological effects, as does the parenteral administration (i.e. as be characterized by the "skunk-like" odor). However, TTFD can be effective, although not to the extent of rectal administration, given both orally and intravenously.

More specifically, tetrahydrofurfuryl disulfide is administered, in any of the above stated embodiments, in an effective amount of 50 mg twice a day. In another embodiment, an effective dosage administered to children of 50 mg three times per day, would also suffice in the practice of the invention. Other dosages are also contemplated by the invention. The inventors have administered, for therapeutic purposes, such as thiamine deficiency, dosages of TTFD as low as 5 mg/day and as high as 5000 mg/day.

For adults, the TTFD can be administered, for example, at 2 mg/kg of body weight per day.

TTFD is effective in treating autism at a dosage of 50 mg two or three times per day in both children and adults. Other dosages can be effective. Optimum dosage levels can be readily determined by one of ordinary skill in the art in view of this disclosure.

The following example describing a pilot study where TTFD was used to treat autistic children, is for illustrative properties only and should not be used to limit the invention.

EXAMPLE 1

In a pilot study, ten autistic children, eight boys and two girls, were administered 50 mg of TTFD twice a day through a rectal suppository for a two-month trial period. All the patients were previously diagnosed with autism as defined by those in the field. Parents were asked to fill in a symptom check form to assess the symptoms of the autistic children by giving a numerical score as to severity.

Two forms were used to obtain clinical information to confirm the response to treatment. Both forms are scored by computer and were designed by the Autism Research Institute specifically for research of this spectrum of disease. The first form, Form E2, is a diagnostic tool that allocates points on a symptomatic basis. The higher the score, the closer the patient comes to being considered a classic case of autism. The common form of autism that is occurring within the pilot test group seldom reaches the score that indicates classic autism, defined as the inability of a person to relate herself in the ordinary way to people and situations from the beginning of life.

The second form, the ATEC (Autism Treatment Evaluation Checklist) form, also allocates points on a symptomatic basis. As treatment proceeds, a decreasing score in subsequent forms indicates clinical improvement. By plotting the E2 scores against the ATEC scores, it was observed that patients with the best clinical improvement were those more severely affected by the disease. In addition to completing the forms based on patient behavior, physiological changes were also measured.

Biochemical Studies

Random urine specimens were collected from each child at the outset of the study, at one month after treatment and again after two months. Each sample was analyzed for the SH- reactive metals, including arsenic, lead, mercury, cadmium; total protein; sulfate; thiosulfate and thiocyanate.

Analysis of SH- reactive metals

Urinary arsenic, lead and cadmium for 19 age-matched controls and 10 autistic patients were measured using a Leeman Direct Reading Echelle inductively coiled plasma emission spectrometer. Mercury was analyzed using a Leeman PS 200II automated analyzer.

Analysis of Sulfate, Sulfite, Thiosulfate, Thiocyanate and Total Protein

Urine samples were collected in the presence of 10% thymol in isopropanol (0.5 ml/100 ml urine) and stored at $-20°$ C. until time of analysis. A third party coded the samples for a blind analysis.

Hair Analysis

One gram of hair was cut from the nape of the neck of each patient. The hair was then dissolved in trace metal-free nitric acid and diluted with 10 ml of deionized water. The analysis was performed with a Leeman PS 2000 inductively coiled emission plasma spectrometer and the samples were compared to standards traceable to the National Bureau of Standards.

Erythrocyte Transketolase

Erythrocyte transketolase studies were performed at the outset and again after 2 months of treatment.

Results

FIG. 1 shows the score of each child on the E2 form. The vertical axis represents the score as calculated by the E2 form for each patient. The horizontal axis represents each of the 10 patients in order of severity of symptomatology. Absence of a bar indicates a score of zero for that category. Scores ranged from −31, representing the child least resembling the autistic spectrum, to +25 or higher, the patient most closely resembling the symptoms of classic autism. Scores of −15 or higher and rarely running as high as +31 or +40 are usually regarded as "autism" in the common form.

Figure 2:
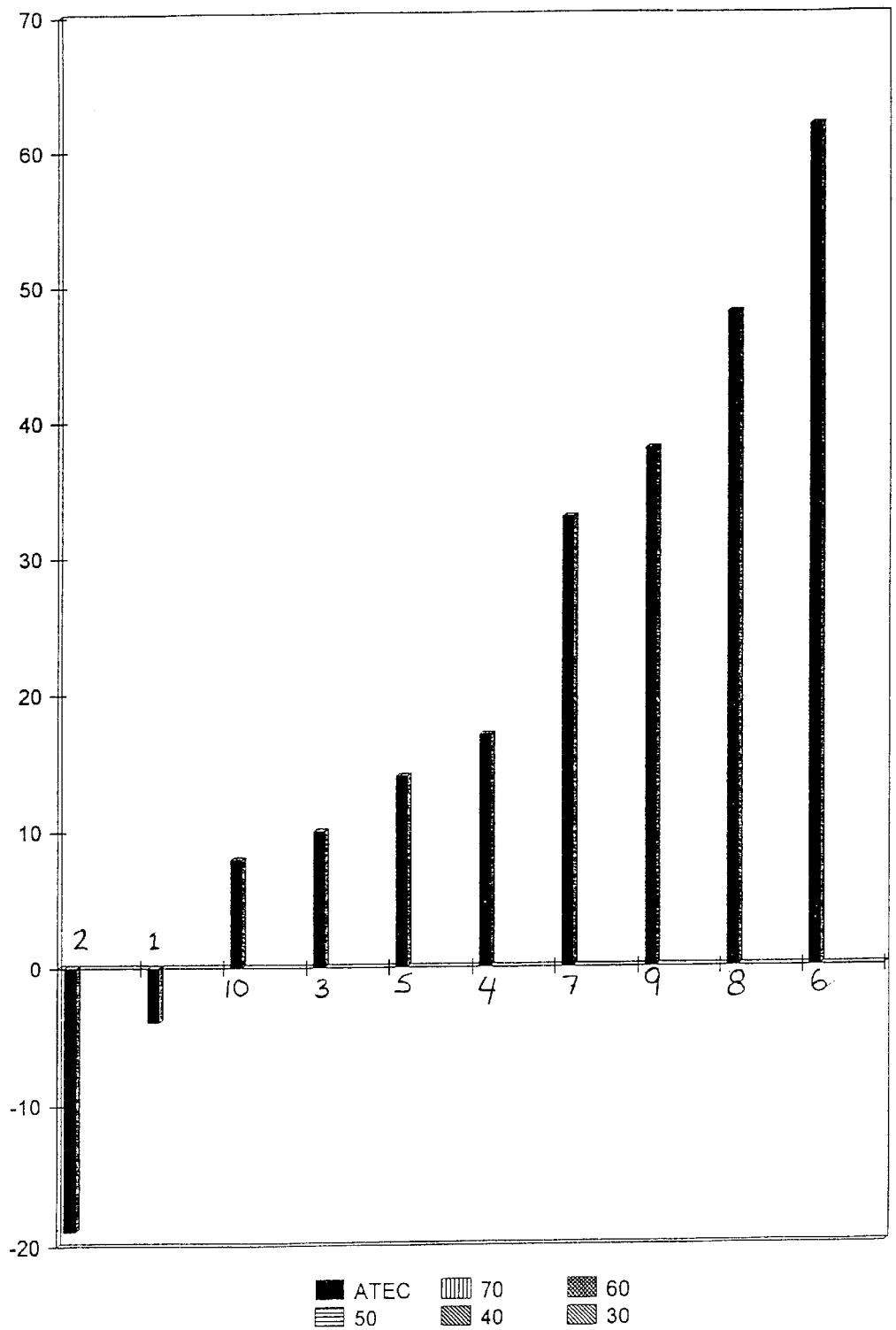
FIG. 2 is yet another graph of the results obtained in the pilot study. The graph shows the 10 patients clinical improvement as a result of treatment with TTFD.

FIG. 2 shows the improvement scores for each child as measured by the ATEC forms after treatement with TTFD was completed. Clinical improvement, as shown by the bars, is obtained by subtracting the final ATEC score from that calculated at the outset of the study. The first two patients whose scores were negative, as shown in the figure, were those that had the highest functional rating calculated from the E2 forms.

Figure 3:
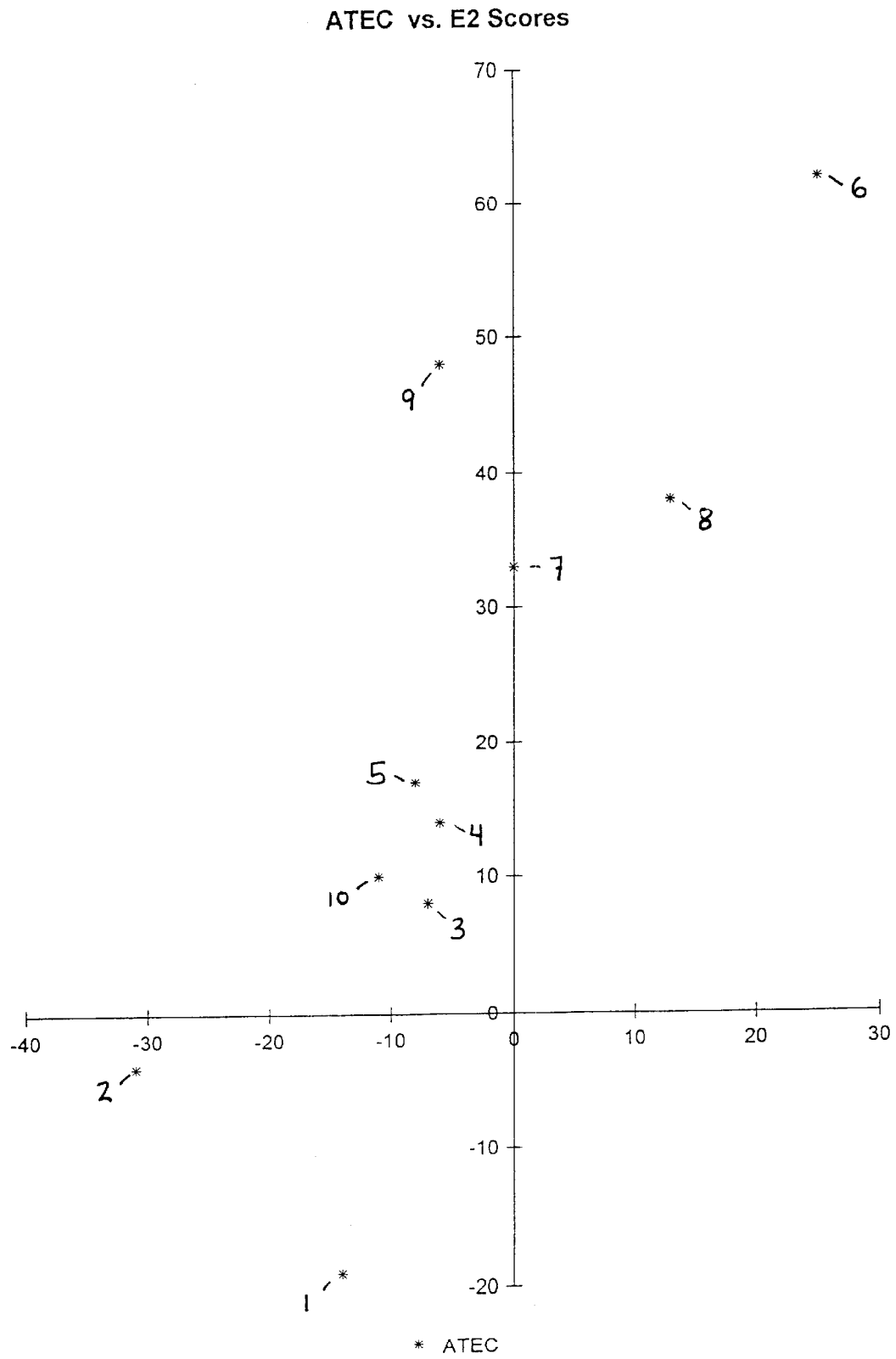
FIG. 3 is a third graph of the results from the pilot study. This graph shows a plot of the patients Autism Treatment Evaluation Checklist improvement score versus their E2 scores.

FIG. 3 shows the result of plotting the E2 scores against the ATEC improvement scores. The plotting indicates that those children most affected with autism had the greatest clinical response to the treatment (Regression statistics for FIG. 3: Multiple R—0.8204; R square—0.6731; adjusted R square—0.6322; Standard error—15.593). The greatest improvements were noted with the patients whose scores were highest initially. The lowest rating from E2 in the study was a 6-year old girl with seizures but with symptoms that were classified clinically as Persistent Development Delay. In 9 of the patients, the parents reported an odor from their child that was repeatedly described as resembling that from a skunk. In one 4-year old boy the father noted that his son's widely dilated and unresponsive pupils would suddenly constrict for short periods during the treatment with TTFD.

Table 1, below, shows the results from the urine studies. Table I shows the mean concentrations of SH- reactive metals throughout the study. The slight increase in lead did not reach a statistical significance. Nine patients had arsenic as the dominant contaminant.

TABLE I

URINARY SH-REACTIVE METALS (Mcg/g Creatinine)*

| Metal | Subjects | N | Mean Concentration | P value |
|---|---|---|---|---|
| Arsenic | Controls | 19 | 32.5 ± 17 | |
| | Pts 1 | 10 | 76.5 ± 79.7 | <0.005 |
| | Pts 3 | 10 | 52.1 ± 20.3 | <0.001 |
| Mercury | Controls | 19 | 0.286 ± 0.41 | |
| | Pts 1 | 10 | 1.42 ± 2.73 | <0.025 |
| | Pts 3 | 10 | 1.21 ± 1.24 | <0.001 |
| Lead | Controls | 19 | 1.97 ± 2.81 | |
| | Pts 1 | 10 | 2.6 ± 3.2 | NS |
| | Pts 3 | 10 | 3.3 ± 3.8 | NS |
| Cadmium | Controls | 19 | 0.158 ± 0.13 | |
| | Pts 1 | 10 | 1.57 ± 2.31 | <0.005 |
| | Pts 3 | 10 | 0.42 ± 0.49 | <0.005 |

*Table I represents the mean concentrations of arsenic, mercury, lead and cadmium in 10 children with autistic spectrum disorder. Pts 1 represents urine analysis at outset of study and Pts 3 represents urine analysis after two months of treatment with TTFD.

Table II, below, shows the results of analysis of urinary sulfate, sulfite, thiosulfate, thiocyanate and total protein. The pilot study did not show the difference in sulfur metabolites between the urine of autistic patients and controls as reported by Waring and Klovrza in Sulphur Metabolism in Autism, *J. Nutr. Env. Med.*, 2000; 10: 25–32. It should be noted that there may be many different biochemical lesions in different populations of affected children. This does not preclude the effectiveness of TTFD through other energy dependent mechanisms.

TABLE II

URINARY METABOLITES*

| | Controls | Pts 1 | Pts 2 | Pts 3 |
|---|---|---|---|---|
| | | Total Sulfate | | |
| Mean | 7742.7 ± 3789.5 | 6543.1 ± 4524 | 7134.3 ± 4631 | 5946.2 ± 4278 |
| P Value | NS | NS | NS | NS |

TABLE II-continued

URINARY METABOLITES*

|  | Controls | Pts 1 | Pts 2 | Pts 3 |
|---|---|---|---|---|
|  |  | Total Sulfite |  |  |
| Mean | 50.9 ± 84.6 | 28.1 ± 57.9 | 47.2 ± 77.6 | 16.9 ± 24.7 |
| P value | NS | NS | NS | NS |
|  |  | Total Thiosulfate |  |  |
| Mean | 39.6 ± 26.1 | 25.8 ± 19.3 | 25.8 ± 15.7 | 25.6 ± 24.5 |
| P Value | NS | NS | NS | NS |
|  |  | Total Thiocyanate |  |  |
| Mean | 11.1 ± 14.4 | 24.4 ± 14.4 | 24.9 ± 21.1 | 29.3 ± 28.7 |
| P Value | NS | NS | NS | NS |
|  |  | Total Protein |  |  |
| Mean | 85.9 ± 45.6 | 88 ± 76.8 | 72.3 ± 65.6 | 62.2 ± 44.0 |
| P Value | NS | NS | NS | NS |

*Table II represents the urinary sulfate, sulfite, thiosulfate, thiocyanate and total protein in 10 healthy, age matched children and 10 patients with autistic spectrum disorder.

Table III, below, shows the results of erythrocyte transketolase (TKA), thiamine pyrophosphate effect (TPPE) and hair analysis for arsenic concentration at the beginning and end of the study. The increase in TPPE from 5% to 30% in one child is unexplained.

TABLE III

| Patient | TKA IUM/l/min | | TPPE % | | HAIR ARSENIC PPM | |
|---|---|---|---|---|---|---|
|  | 1st | 2nd | 1st | 2nd | 1st | 2nd |
| 1 | 55 | 77 | 9 | 4 | 0.09 | 2.19 |
| 2 | 74 | 90 | 8 | 0 | 1.5 | 2.22 |
| 3 | 77 | 80 | 18 | 8 | 2.48 | 1.37 |
| 4 | 74 | 83 | 5 | 11 | 1.55 | 3.5 |
| 5 | 87 | 66 | 3 | 11 | 1.66 | 1.08 |
| 6 | 43 | 76 | 21 | 4 | 2.28 | 1.81 |
| 7 | 80 | NT | 15 | NT | 2.07 | 3.18 |
| 8 | 56 | 89 | 41 | 9 | 0.76 | 2.62 |
| 9 | 66 | NT | 5 | NT | 0.81 | 1.68 |
| 10 | 86 | 81 | 5 | 30 | 2.97 | 3.8 |

Mean value for $1^{st}$ and $2^{nd}$ hair arsenic concentrations:
$1^{st}$: 1.62 ± 0.88 P Value
$2^{nd}$: 2.35 ± 0.91 NS Results of the laboratory study showed that 9 out of the 10 subjects were found to have an high concentration of arsenic in their urine. After 1 month of treatment, the urinary arsenic tended to increase followed by a decline at completion of the study. This suggests that arsenic may play an important role in autism and that TTFD may be instrumental in causing the arsenic to be excreted. An increased amount of lead, cadmium and mercury, respectively, was seen in some of the children's urine but this was much less consistent than the concentrations of arsenic found.

Eight of the 10 subjects in the pilot study showed clinical improvement in their autistic disorder while being treated with TTFD. Each parent described the odor exuded by the subject during the study as "skunk-like." The "skunk-like" odor suggests that one of the metabolic products of TTFD given under these conditions is a mercaptan, a sulfur containing metabolite. TTFD is not known for giving off this odor when administered by mouth for other purposes, like thiamine deficiency.

Arsenic, lead, mercury and cadmium are toxic substances having some biological commonality. All are known as SH-reactive, meaning that they react with SH radicals that play a vital part in oxidative sulfur metabolism. The finding of arsenic in the urine of these children, as well as sporadic occurrence of other SH-reactive metals, suggests their importance in the underlying cause of autism in certain cases. Proving their removal by the use of TTFD might be an extremely important objective. The clinical history of TTFD suggests, however, that it has properties that exceed that of merely extracting heavy metals. Its administration may result in significant increases in the phosphorylated components of thiamine, including thiamine triphosphate, that have a vital part in the energy metabolism in brain and central nervous system tissue.

A very significant clinical response was observed in this preliminary study. TTFD given parentarally (e.g., by rectal suppository) is believed to produce a metabolic effect that is not experienced as greatly when given orally. A few children with autism have been exposed to a dermal preparation since the study has been completed. Parents have observed the "skunk-like" odor. In addition, an immediate improvement in the child's condition was noted. For example, improvement was observed in the child's ability to sleep.

Many modifications and variations of the invention will be apparent to those of ordinary skill in the art in light of the foregoing disclosure. Therefore, it is to be understood that, within the scope of the appended claims, the invention can be practiced otherwise than has been specifically shown and described.

We claim:

1. A method of treating autism comprising administering a therapeutically effective amount of a lipid-soluble thiamine derivative to a person in need of such treatment.

2. The method according to claim 1 wherein said lipid-soluble thiamine derivative is tetrahydrofurfuryl disulfide.

3. The method according to claim 1 wherein said lipid-soluble thiamine derivative is administered orally.

4. The method according to claim 1 comprising rectally administering said lipid-soluble thiamine derivative in the form of a suppository.

5. The method according to claim 1 comprising parenterally administering said lipid-soluble thiamine derivative.

6. The method according to claim 5 wherein said parenteral administration comprises transdermal application of said lipid-soluble thiamine derivative and a pharmaceutically acceptable carrier.

7. The method according to claim 6 wherein said parenteral administration comprises sublingual application of said lipid-soluble thiamine derivative.

8. The method according to claim 1 wherein said lipid-soluble thiamine derivative is administered to a child in need of such treatment.

9. The method according to claim 1 comprising administering said lipid-soluble thiamine derivative at least once a day, wherein the total daily dosage is up to 100 mg per day.

10. A method of treating autism comprising administering a therapeutically effective amount of a lipid-soluble thiamine derivative to a child in need of such treatment.

11. The method according to claim 10 wherein said lipid-soluble thiamine derivative is tetrahydrofurfuryl disulfide.

12. A method of treating autism comprising rectally administering a therapeutically effective amount of a lipid-soluble thiamine derivative to a child in need of such treatment.

13. A method of treating autism comprising rectally administering a suppository comprising a therapeutically effective amount of a lipid-soluble thiamine compound to a child in need of such treatment.

14. The method of claim 13 wherein said lipid-soluble thiamine compound comprises tetrahydrofurfuryl disulfide.

* * * * *